United States Patent [19]

Hoehn

[11] 4,307,105

[45] Dec. 22, 1981

[54] IMIDAZOLYLETHOXYMETHYL DERIVATIVES OF THIAZOLE

[75] Inventor: Hans Hoehn, Tegernheim, Fed. Rep. of Germany

[73] Assignee: E. R. Squibb & Sons, Inc., Princeton, N.J.

[21] Appl. No.: 54,544

[22] Filed: Jul. 5, 1979

[51] Int. Cl.³ .......................................... C07D 277/20
[52] U.S. Cl. .................... 424/270; 548/203; 548/205
[58] Field of Search .................. 548/185, 203, 205; 424/270

[56] References Cited

U.S. PATENT DOCUMENTS

| 3,821,376 | 6/1974 | Bayer | 424/245 |
|---|---|---|---|
| 4,062,966 | 12/1977 | Gymer | 548/205 |
| 4,085,209 | 4/1978 | Miller | 424/245 |
| 4,108,990 | 8/1978 | Plum | 424/245 |
| 4,108,994 | 8/1978 | Poitteuin | 424/250 |

FOREIGN PATENT DOCUMENTS 1511390  5/1978  United Kingdom .

OTHER PUBLICATIONS

Chem. Abs.-Alexander, 87:117861u.
Zirngibl, L. CA 88:89673j.

Primary Examiner—Nicholas S. Rizzo
Attorney, Agent, or Firm—Lawrence S. Levinson; Burton Rodney

[57] ABSTRACT

New imidazolylethoxymethyl derivatives of thiazole are provided having the general formula

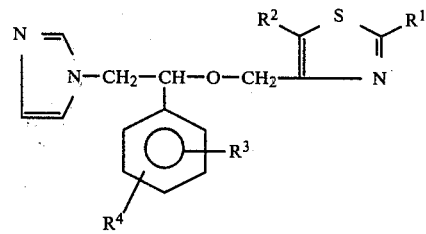

wherein
$R^1$ is hydrogen, lower alkyl, lower alkoxy-lower alkyl, phenoxy-lower alkyl, phenyl-lower alkyl or substituted or unsubstituted phenyl;
$R^2$ is hydrogen or halogen;
$R^3$ and $R^4$ are the same or different and are hydrogen, lower alkyl, lower alkoxy or halogen.

The above compounds and their salts are useful as antifungal and antibacterial agents.

8 Claims, No Drawings

IMIDAZOLYLETHOXYMETHYL DERIVATIVES OF THIAZOLE

SUMMARY OF THE INVENTION

This invention relates to new 4-[2-(1H-imidazol-1-yl)ethoxy]methylthiazoles and the acid addition salts of these compounds having the general formula

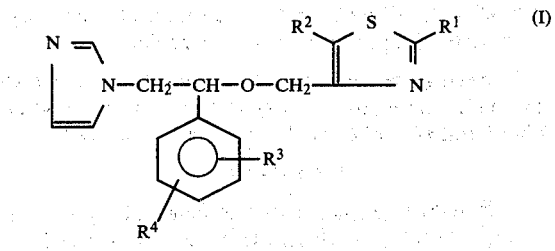

wherein
- $R^1$ is hydrogen, lower alkyl, lower alkoxy-lower alkyl, phenoxy-lower alkyl, phenyl-lower alkyl, or unsubstituted or substituted phenyl, wherein the phenyl group bears one halogen, hydroxy, lower alkoxy, lower alkyl, lower alkylthio, cyano or nitro group;
- $R^2$ is hydrogen or halogen;
- $R^3$ and $R^4$ are the same or different and each is hydrogen, lower alkyl, lower alkoxy or halogen.

The above compounds of formula I and their salts are useful as antifungal and antibacterial agents.

DETAILED DESCRIPTION OF THE INVENTION

In formula I the lower alkyl groups include straight or branched chain hydrocarbon groups containing 1 to 7 carbon atoms. Examples of the type of groups contemplated are methyl, ethyl, propyl, isopropyl, etc. The lower alkoxy and lower alkylthio groups include such lower alkyl groups bonded to an oxygen or sulfur, respectively, e.g., methoxy, ethoxy, propoxy, butoxy, t-butoxy, methylthio, ethylthio, propylthio, butylthio, isobutylthio. In all of these radicals the $C_1$–$C_4$, especially the $C_1$–$C_2$ members, are preferred.

The halogens are the four common halogens, chlorine and bromine being preferred in that order.

The substituted phenyl groups refer to phenyl rings bearing one of the simple substituents named, which are of the same character as described above. Unsubstituted phenyl is preferred.

Preferred embodiments of the invention are compounds of formula I wherein $R^1$ is phenyl, halophenyl, or lower alkyl, $R^2$ is hydrogen or bromine, and $R^3$ and $R^4$ each is hydrogen or halogen. Especially preferred are those compounds of formula I wherein $R^1$ is phenyl, p-chlorophenyl, methyl or propyl, $R^2$ is hydrogen or bromine, and $R^3$ and $R^4$ are each hydrogen or chlorine. The hydrohalide salts and especially the hydrochloride salt, are also preferred.

The compounds of formula I are prepared by etherizing of a 1-phenyl-2(1H-imidazol-1-yl)ethanol of the formula

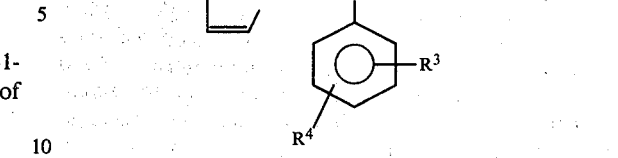

with an appropriate reactive ester of the formula

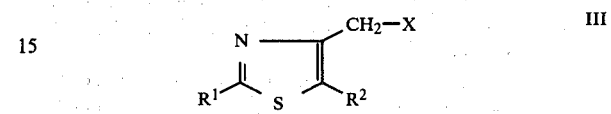

wherein X is a reactive ester function, such as halo, mesyl, tosyl, or the like.

Reactive thiazolyl esters of the formula III are disclosed in the literature, for example, in *The Chemistry of Heterocyclic Compounds*, Vol. 34, Thiazole and Its Derivatives, Part 1, edited by J. V. Metzger, p. 185, John Wiley and Sons, N.Y. 1979, and are accessible by reaction of bishaloketones of the formula IV

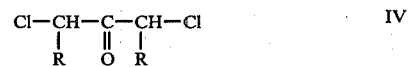

wherein R is hydrogen, lower alkyl, phenyl, phenyl-lower alkyl, with an appropriately substituted thioamide of the formula

Additional experimental details are found in the illustrative examples below.

The compounds of formula I form salts which are also part of this invention. The salts include acid-addition salts, particularly the non-toxic, physiologically acceptable members. The compounds of formula I form salts by reaction with a variety of inorganic and organic acids providing acid addition salts including, for example, hydrohalides (especially hydrochloride and hydrobromide), sulfate, nitrate, borate, phosphate, oxalate, tartrate, maleate, citrate, acetate, ascorbate, succinate, benzenesulfonate, methanesulfonate, cyclohexanesulfamate and toluene-sulfonate. The acid addition salts frequently provide a convenient means for isolating the product, e.g., by forming and precipitating the salt in the appropriate medium in which the salt is insoluble, then after separation of the salt, neutralizing with a base such as barium hydroxide or sodium hydroxide, to obtain the free base of formula I. Other salts may then be formed from the free base by reaction with an equivalent of acid having the desired anion.

The new compounds of formula I and their salts are useful as antimicrobial agents, particularly as antifungal agents, and can be used to combat infections in various mammalian species, such as mice, rats, dogs, guinea pigs and the like, due particularly to organisms such as *Candida albicans* as well as organisms such as *Trichomonas*

*vaginalis* or *Trichophyton mentagrophytes.* For example, a compound or mixture of compounds of formula I or physiologically acceptable acid addition salt thereof can be administered orally to an infected animal, e.g., to a mouse, in an amount of about 5 to 25 mg/kg/day in 2 to 4 divided doses. These may be conventionally formulated in a tablet, capsule or elixir containing about 10 to 250 mg per dosage unit, by compounding the active substance or substances with the conventional excipient, vehicle, binder, preservative, flavor, etc. as called for by accepted pharmaceutical practice. Preferably they are applied topically, e.g., intravaginally in a lotion or in a conventional cream base at a concentration of about 0.01 to 3 percent by weight for a period of 3 to 7 days, 2 to 4 times daily.

The following examples are illustrative of the invention. They represent particularly preferred embodiments and also serve as models for the preparation of other members of the group. All temperatures are on the Celsius scale.

EXAMPLE 1

4-[[1-(2,4-Dichlorophenyl)-2-(1H-imidazol-1-yl)-ethoxy]methyl]-2-methylthiazole, hydrochloride (1:1)

(a) 4-Chloromethyl-2-methylthiazole, hydrochloride (1:1)

25.4 g of 1,3-dichloroacetone (0.2 mol) and 15 g of thioacetamide (0.2 mol), dissolved in 200 ml of absolute alcohol are stirred at 60°-70° for two hours. Subsequently, the solution is filtered and after evaporation in vacuo the residue is treated with 200 ml of ether. The 4-chloromethyl-2-methylthiazole, hydrochloride (32.8 g=89%) is filtered off and recrystallized from absolute alcohol (refrigerator); m.p. 168°-170° C.

(b) 4-[[1-(2,4-Dichlorophenyl)-2-(1H-imidazol-1-yl)-ethoxy]methyl]-2-methylthiazole, hydrochloride (1:1)

In a three-necked flask, fitted with stirrer, reflux condenser and gas inlet tube, 44 g of sodium hydroxide (1.1 mol) and 50 ml of water are introduced. While passing nitrogen through the flask, the solution is cooled to 45° and then 11.6 g of (1-(2,4-dichlorophenyl)-2-(1H-imidazol-1-yl)ethanol (0.045 mol) [prepared by the method of *J. Med. Chem.* 12, 784, (1969)], 0.75 g of benzyltrimethylammonium chloride and 150 ml of tetrahydrofuran are added. To the mixture, which is warmed to 50°, 8.3 g of 4-chloromethyl-2-methylthiazole, hydrochloride (0.045 mol) are added and the mixture is stirred vigorously for two hours at 60°. The filtered biphasic solution is transferred into a separating funnel, the lower aqueous sodium hydroxide is extracted with 10 ml of tetrahydrofuran. The combined tetrahydrofuran layers are treated with charcoal and after drying with sodium sulphate, the solvent is evaporated in vacuo. The resulting oily product, dissolved in 250 ml of ether, is allowed to stand overnight in a refrigerator, by which operation unreacted 1-(2,4-dichlorophenyl)-2-(1H-imidazol-1-yl)ethanol is separated. Filtering off and addition of ethereal hydrochloric acid to the clear ethereal solution yields the hydrochloride of 4-[[1-(2,4-dichlorophenyl)-2-(1H-imidazol-1-yl)ethoxy]methyl]-2-methylthiazole. Yield: 12.8 g (71%). Recrystallization from acetonitrile gives a hydrochloride with the m.p. of 194°-196° C.

EXAMPLE 2

4-[[1-(2,4-Dichlorophenyl)-2-(1H-imidazol-1-yl)-ethoxy]methyl]-2-propylthiazole, hydrochloride (1:1)

(a) 4-Chloromethyl-2-propylthiazole, hydrochloride

Following the procedure of Example 1a, the above compound is recrystallized from ethylacetate, m.p. 89°-90° C.

(b) 4-[[1-(2,4-Dichlorophenyl)-2-(1H-imidazol-1-yl)ethoxy]methyl]-2-propylthiazole, hydrochloride (1:1)

Following the procedure according to Example 1b, the title compound recrystallized from absolute ethanol/ethyl acetate is obtained, m.p. 118°-120° C.

EXAMPLE 3

4-[[1-(2,4-Dichlorophenyl)-2-(1H-imidazol-1-yl)-ethoxy]methyl]-2-phenylthiazole, hydrochloride (1:1)

Following the procedure of Example 1b, 4-chloromethyl-2-phenylthiazole (prepared according to Example 1a from thiobenzamide and 1,3-dichloroacetone, m.p. 134°-136° C. (absolute alcohol/ethylacetate), is reacted with 1-(2,4-dichlorophenyl)-2-(1H-imidazol-1-yl)ethanol to obtain the title compound, m.p. 204°-205° C. (absolute alcohol/ethyl acetate).

EXAMPLE 4

2-(4-Chlorophenyl)-4-[[1-(2,4-dichlorophenyl)-2-(1H-imidazol-1-yl)ethoxy]methyl]thiazole, hydrochloride (1:1)

Following the procedure of Example 1b, 4-chloromethyl-2-(4-chlorophenyl)thiazole (m.p. 66°) is reacted with 1-(2,4-dichlorophenyl)-2-(1H-imidazol-1-yl)ethanol to yield the title compound, m.p. 108°-110° C. (acetonitrile).

EXAMPLE 5

5-Bromo-4-[[1-(2,4-dichlorophenyl)-2-(1H-imidazol-1-yl)ethoxy]methyl]-2-methylthiazole, hydrochloride (1:1)

(a) 5-Bromo-4-chloromethyl-2-methylthiazole

To 11 g of 4-chloromethyl-2-methylthiazole, hydrochloride (0.06 mol), dissolved in 150 ml of glacial acetic acid are added while stirring, 11.5 g of anhydrous sodium acetate (0.14 mol) and at 45°-50°, 9.6 g of bromine (0.12 mol) in 50 ml of glacial acetic acid. Stirring is continued for an additional 2.5 hours at 60°-80° C. Then the solution is evaporated in vacuo to dryness and the residual product is extracted with ether. Evaporation of the solvent gives 8.3 g oil which is then dissolved in hexane. Charcoal treatment, evaporation of the solvent, dissolving of the oil again in 100 ml of ether and addition of ethereal hydrochloric acid, yield the hydrochloride. Yield: 6.5 g (41%), m.p. 154°-156° C.

(b) 5-Bromo-4-[[1-(2,4-dichlorophenyl)-2-(1H-imidazol-1-yl)ethoxy]methyl]-2-methylthiazole, hydrochloride (1:1)

Following the procedure of Example 1b, reaction of 5-bromo-4-chloromethyl-2-methylthiazole and 1-(2,4-dichlorophenyl)-2-(1H-imidazol-1-yl)ethanol, yields the title compound, m.p. 247°-248° C. (absolute ethanol).

EXAMPLE 6

5-Bromo-4-[[1-(2,4-dichlorophenyl)-2-(1H-imidazol-1-yl)ethoxy]methyl]-2-phenylthiazole, hydrochloride (1:1)

Following the procedure of Example 1b, reaction of 5-bromo-4-chloromethyl-2-phenylthiazole (prepared according to Example 5a, m.p. 86°–87° (hexane)), with 1-(2,4-dichlorophenyl)-2-(1H-imidazol-1-yl)ethanol, yields the title compound, m.p. 238°–240° C. (absolute ethanol).

EXAMPLES 7 TO 25

The following additional compounds shown in Column III of Table A set out below are produced by the procedure of Example 1, by substituting for 1-(2,4-dichlorophenyl)-2-(1H-imidazol-1-yl)ethanol the compound shown in Column I of Table A below, and substituting for 4-chloromethyl-2-methylthiazole, hydrochloride, the compound shown in Column II.

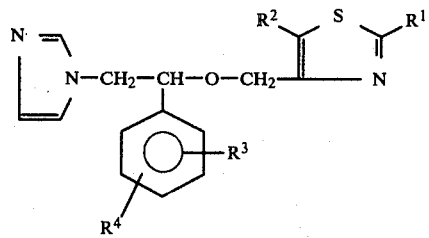

wherein
R$^1$ is phenyl or substituted phenyl, wherein the phenyl bears one halogen, hydroxy, lower alkoxy, lower alkyl, lower alkylthio, cyano or nitro group;
R$^2$ is hydrogen;
R$^3$ and R$^4$ are the same or different and each is hydrogen, lower alkyl, lower alkoxy or halogen;
and non-toxic physiologically acceptable acid addition salts thereof.

TABLE A

| | Column I | | | | | Column II | | | Column III | | | |
|---|---|---|---|---|---|---|---|---|---|---|---|---|
| Ex. No. | R$^4$ (position) | R$^3$ (position) | R$^1$ | R$^2$ | X | | | | R$^4$ (position) | R$^3$ (position) | R$^1$ | R$^2$ |
| 7. | H | H | H | H | Cl | | | | as in Column I | | as in Column II | |
| 8. | H | H | CH$_3$ | H | Br | | | | | | | |
| 9. | H | H | C$_6$H$_5$ | H | Cl | | | | | | | |
| 10. | CH$_3$(2) | CH$_3$(4) | H | H | Cl | | | | | | | |
| 11. | CH$_3$O(3) | CH$_3$O(5) | C$_2$H$_5$ | Br | Br | | | | | | | |
| 12. | Cl(2) | H | CH$_3$OCH$_2$ | H | mesyl | | | | | | | |
| 13. | Br(3) | H | C$_6$H$_4$OCH$_2$ | Cl | Cl | | | | | | | |
| 14. | C$_2$H$_5$(2) | C$_2$H$_5$(4) | C$_6$H$_4$CH$_2$ | Br | Cl | | | | | | | |
| 15. | C$_2$H$_5$(4) | H | p-OH—C$_6$H$_4$ | H | Br | | | | | | | |
| 16. | Br(2) | Br(4) | o-CH$_3$—C$_6$H$_4$ | Cl | tosyl | | | | | | | |
| 17. | H | CH$_3$(3) | m-C$_2$H$_5$O—C$_6$H$_4$ | Br | Br | | | | | | | |
| 18. | Cl(2) | Cl(4) | p-CH$_2$S—C$_6$H$_4$ | Cl | Cl | | | | | | | |
| 19. | Br(2) | Br(4) | o-CN—C$_6$H$_4$ | Br | Cl | | | | | | | |
| 20. | H | H | p-NO$_2$—C$_6$H$_4$ | H | Cl | | | | | | | |
| 21. | C$_3$H$_7$(2) | C$_3$H$_7$(4) | C$_2$H$_5$OC$_2$H$_4$ | Cl | Br | | | | | | | |
| 22. | CH$_3$(2) | C$_2$H$_5$(4) | C$_6$H$_4$OC$_2$H$_4$ | Br | Cl | | | | | | | |
| 23. | H | H | C$_6$H$_4$C$_2$H$_4$ | H | Cl | | | | | | | |
| 24. | Cl(2) | Cl(4) | C$_6$H$_5$ | H | Cl | | | | | | | |
| 25. | Br(3) | Br(5) | H | Cl | Br | | | | | | | |

What is claimed is:

1. A compound of the formula

2. The compound as defined in claim 1 wherein R$^1$ is phenyl substituted with one halogen.

3. The compound as defined in claim 1 wherein R$^3$ and R$^4$ are halogen.

4. The compound as defined in claim 3 wherein R$^3$ and R$^4$ are each chlorine or bromine.

5. The compound as defined in claim 1 in the form of its hydrochloride salt.

6. The compound as defined in claim 1 having the name 2-(4-chlorophenyl)-4-[[1-(2,4-dichlorophenyl)-2-(1H-imidazol-1-yl)ethoxy]methyl]thiazole or its hydrochloride salt.

7. An antimicrobial composition comprising a compound as defined in claim 1 and a pharmaceutically acceptable carrier therefor.

8. A method for treating bacterial or fungal infections in mammals which comprises administering to a mammalian host an effective amount of a compound as defined in claim 1.

* * * * *